United States Patent
Namanga et al.

(10) Patent No.: US 10,177,321 B2
(45) Date of Patent: Jan. 8, 2019

(54) METAL COMPLEX AND ORGANIC LIGHT-EMITTING COMPONENT

(71) Applicant: OSRAM OLED GmbH, Rebensburg (DE)

(72) Inventors: Jude Eko Namanga, Augsburg (DE); Niels Gerlitzki, Augsburg (DE)

(73) Assignee: OSRAM OLED GmbH, Regensburg (DE)

( * ) Notice: Subject to any disclaimer, the term of this patent is extended or adjusted under 35 U.S.C. 154(b) by 0 days.

(21) Appl. No.: 15/215,355

(22) Filed: Jul. 20, 2016

(65) Prior Publication Data

US 2017/0025623 A1    Jan. 26, 2017

(30) Foreign Application Priority Data

Jul. 24, 2015  (DE) .................. 10 2015 112 133

(51) Int. Cl.
 *H01L 51/00* (2006.01)
 *C07F 15/00* (2006.01)
 (Continued)

(52) U.S. Cl.
 CPC ...... *H01L 51/0085* (2013.01); *C07F 15/0033* (2013.01); *C09K 11/025* (2013.01);
 (Continued)

(58) Field of Classification Search
 CPC combination set(s) only.
 See application file for complete search history.

(56) References Cited

U.S. PATENT DOCUMENTS

| 2008/0096028 A1* | 4/2008 | Wegh ............... C09K 11/06 428/447 |
| 2017/0025624 A1* | 1/2017 | Namanga ........... H01L 51/0072 |
| 2017/0025625 A1* | 1/2017 | Namanga ........... C07F 15/0033 |

FOREIGN PATENT DOCUMENTS

CN    103936791 A    7/2014

OTHER PUBLICATIONS

Bolink, H.J. et al.: "Red Emitting [Ir(CN)2(NN)]+ Complexes Employing Bidentate 2,2':6',2"-Terpyridine Ligands for Light-Emitting Electrochemical Cells," Dalton Transactions, Mar. 28, 2014, pp. 4653-4667, vol. 43.

(Continued)

*Primary Examiner* — Jennifer A Chriss
*Assistant Examiner* — Sean M DeGuire
(74) *Attorney, Agent, or Firm* — Slater Matsil, LLP (57) ABSTRACT

A metal complex and an organic light-emitting component are disclosed. In an embodiment, the metal complex includes the following structural formula I:

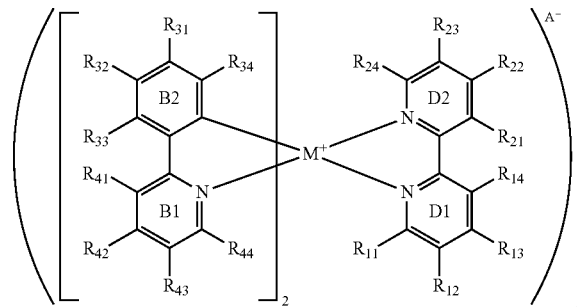

11 Claims, 4 Drawing Sheets

(51) Int. Cl.
C09K 11/02 (2006.01)
C09K 11/06 (2006.01)
H05B 33/14 (2006.01)
H01L 51/50 (2006.01)

(52) U.S. Cl.
CPC .......... C09K 11/06 (2013.01); *H01L 51/0061* (2013.01); *H01L 51/0072* (2013.01); *H05B 33/14* (2013.01); *C09K 2211/1007* (2013.01); *C09K 2211/1011* (2013.01); *C09K 2211/1029* (2013.01); *C09K 2211/185* (2013.01); *H01L 51/5012* (2013.01); *H01L 51/5016* (2013.01); *H01L 51/5032* (2013.01)

(56) References Cited

OTHER PUBLICATIONS

Bolink, H.J. et al.: "Red-Light-Emitting Electrochemical Cell Using a Polypyridyl Iridium (III) Polymer," Dalton Transactions, Sep. 2009, pp. 9787-9793, Issue 44.

Bolink, H.J. et al.: "Luminescent Ionic Transition-Metal Complexes for Light-Emitting Electrochemical Cells," Wiley-VCH, Angew. Chem. Int. Edition, Aug. 2012, pp. 8178-8211, vol. 51.

Chun, L. et al.: "A General and Highly Efficient Method for the Construction of Aryl-Substituted N-Heteroarenes," European Journal of Organic Chemistry, Oct. 2010, pp. 5548-5551, vol. 29.

Dong Y.P. et al.: "Electrogenerated Chemiluminescence of a cationic Cyclometalated Iridium Complex-Nafion Modified Electrode in Neutral Aqueous Solution," Journal of Luminescence, Apr. 2013, pp. 165-171, vol. 136.

Duan, L. et al.: "Solid-State Light-Emitting Electrochemical Cells Based on Ionic Iridium (III) Complexes," Journal of Materials Chemistry, Jan. 2012, pp. 4206-4215, vol. 22.

Holder, E. et al.: "New Trends in Use of Transition Metal-Ligand Complexes for Applications in Electroluminescent Devices," Advanced Materials, Apr. 2005, pp. 1109-1121, vol. 17.

Li, Z. et al.; "Nonlinear Absorbing Cationic Bipyridyl Iridium (III) Complexes Bearing Cyclometalating Ligands With Different Degrees of TT-Conjugation: Synthesis, Photophysics, and Reverse Saturable Absorption," Journal of Physical Chemistry, Dec. 11, 2014, pp. 28764-28775, vol. 118, Issue 49.

Liao, C. et al.: "Improving the Balance of Carrier Mobilities of Host-Guest Solid-State Light-Emitting Electrochemical Cells," Physical Chemistry Chemical Physics, Nov. 2011, pp. 1262-1269, vol. 14.

Slinker, J. et al.: "Efficient Yellow Electroluminescence From a Single Layer of a Cyclometalated Iridium Complex," J. Am. Chemistry Society, Feb. 17, 2004, pp. 2763-2767, vol. 126, No. 9.

Smith, R. et al.; "Cyclometalated Cinchophen Ligands on Iridium (III): Towards Water-Soluble Complexes With Visible Luminescence," Journal of the Royal Society of Chemistry, Dalton Transactions, Apr. 2013, pp. 10347-10357, vol. 42.

Su, H.C. et al.: "Solid-State White Light-Emitting Electrochemical Cells Using Iridium-Based Cationic Transition Metal Complexes," Journal American Chemical Society, Feb. 27, 2008, pp. 3413-3419, vol. 130, Issue 11.

Tamayo, A. et al.: "Cationic Bis-Cyclometalated Iridium (III) Diimine Complexes and Their Use in Efficient Blue, Green, and Red Electroluminescent Devices," Inorganic Chemistry, Nov. 3, 2005, pp. 8723-8732, vol. 44, No. 24.

Zhang, J. et al.: " Efficient Light-Emitting Electrochemical Cells (LECs) Based on Ionic Iridium (III) Complexes With 1,3,4-Oxadiazole Ligands," Advanced Functional Materials, Apr. 2013, pp. 4667-4677, vol. 23, Issue 37.

Zhao, Q. et al.: "Series of New Cationic Iridium (III) Complexes With Tunable Emission Wavelength and Excited State Properties: Structures, Theoretical Calculations, and Photophysical and Electrochemical Properties," Inorganic Chemistry, Jul. 11, 2006, pp. 6152-6160, vol. 45, No. 16.

Zhao, Q. et al.; "Cationic Iridium (III) Complexes With Tunable Emission Color as Phosphorescent Dyes for Live Cell Imaging," Organometallics Article, Mar. 2010, pp. 1085-1091.

* cited by examiner

METAL COMPLEX AND ORGANIC LIGHT-EMITTING COMPONENT

This patent application claims the priority of German patent application 10 2015 112 133.6, filed Jul. 24, 2015, which is incorporated herein by reference in its entirety.

TECHNICAL FIELD

The invention relates to a metal complex. The invention further relates to an organic light-emitting component.

BACKGROUND

Organic light-emitting components, especially organic light-emitting electrochemical cells (OLECs or LECs), include metal complexes, especially ionic transition metal complexes (iTMCs), as emitter materials, which can emit preferentially in the blue, sky blue, green, yellow-green, yellow, orange or red spectral region. However, these emitter materials are of low structural stability during the operation of the organic light-emitting component, and so the organic light-emitting component has a short lifetime.

SUMMARY OF THE INVENTION

Embodiments of the invention provide a structurally stable metal complex. More particularly, the metal complex is stable to degradation and/or at high temperatures and/or over a long period. Further embodiments of the invention provide a stable organic light-emitting component. More particularly, the component has a long lifetime with equal or high luminescence compared to components known to date that comprise conventional metal complexes.

In at least one embodiment, the metal complex has the structural formula I:

where:

M is a transition metal having an atomic number greater than 40, the B2 ring is at least one aromatic or heteroaromatic, the B1 ring, the D1 ring and the D2 ring are each at least one nitrogen-containing ring, $A^-$ is a monovalent anion, $R_{31}$, $R_{32}$, $R_{33}$, $R_{34}$ are each independently selected from a group comprising —H, —OH, —$R_{50}$, -phenyl, —$OCOR_{60}$, —$NHCOR_{70}$, —$OR_{80}$, —$NR_{90}R_{100}$, —$NHR_{110}$, —C≡, —C═C—, —C═C—, —C and —$NH_2$, where $R_{50}$, $R_{60}$, $R_{70}$, $R_{80}$, $R_{90}$, $R_{100}$, $R_{110}$ are each independently selected from a group comprising unbranched saturated hydrocarbon —C≡, —C═C, —C═C—, —C chains having one to 20 carbon atoms, branched saturated hydrocarbon chains having one to 20 carbon atoms, unbranched unsaturated hydrocarbon chains having one to 20 carbon atoms, branched unsaturated hydrocarbon chains having one to 20 carbon atoms, aromatic rings and nonaromatic rings, $R_{41}$, $R_{42}$, $R_{43}$, $R_{44}$ are each independently selected from a group comprising —H, —I, —Cl, —Br, —F, —$NO_2$, $N^+R_{120}R_{130}R_{140}$, —$SO_3R_{150}$, —CN, —COCl, —$COOR_{160}$, —C≡, —C═C, —C═C—, —C, —$CR_{170}R_{180}OH$, —$CR_{190}O$ and —CHO, where at least one of the $R_{41}$, $R_{42}$, $R_{43}$ and $R_{44}$ radicals is at least one electron-withdrawing substituent, where $R_{120}$, $R_{130}$, $R_{140}$, $R_{150}$, $R_{160}$, $R_{170}$, $R_{180}$, $R_{190}$ are each independently selected from a group comprising unbranched saturated hydrocarbon chains having one to 20 carbon atoms, branched saturated hydrocarbon chains having one to 20 carbon atoms and cyclic rings having 3 to 20 carbon atoms, $R_{11}$, $R_{12}$, $R_{13}$, $R_{14}$, $R_{21}$, $R_{22}$, $R_{23}$, $R_{24}$ are either each independently selected from a group comprising —H, —OH, —$R_{50}$, -phenyl, —$OCOR_{60}$, —$NHCOR_{70}$, —$OR_{80}$, —$NR_{90}R_{100}$, —$NHR_{110}$, —C≡, —C═C, —C═C—, —C and —$NH_2$ or each independently selected from a group comprising —H, —I, —Cl, —Br, —F, $N^+R_{120}R_{130}R_{140}$, —$SO_3R_{150}$, —CN, —COCl, —$NO_2$, —$COOR_{160}$, —$CR_{170}R_{180}OH$, —$CR_{190}O$ and —CHO.

More particularly, —CHO means an aldehyde group and —COH a hydroxyl group substituted on a carbon.

"Metal complex" or Metal complex compound here and hereinafter is understood to mean a chemical compound having a central atom of a transition metal M which has gaps in its electron configuration and is surrounded by at least one or more than one molecule or ion, also called ligands. The central atom may bear a positive charge ($M^+$). The ligands each provide at least one free electron pair for the formation of the metal complex. The metal complex especially forms six coordinate bonds to the ligands. The ligands may be monodentate or polydentate, for example bidentate. More particularly, bonds are formed from the central atom M to the B1, B2, D1 and D2 rings. Since the B1 and B2 rings are present twice in the metal complex, represented by the index 2 in the structural formula I, the result is six bonds from the respective rings to the central atom M. More particularly, the B1, D1 and D2 rings each coordinate via the nitrogen of the corresponding ring to M. More particularly, the respective B2 ring coordinates via a carbon in the B2 ring to M.

In at least one embodiment, M is a transition metal having an atomic number greater than 40. Atomic number refers to the number of protons in the atomic nucleus of the chemical transition metal. More particularly, M is a transition metal selected from groups 8 to 10 of the Periodic Table. In various embodiments, M is selected from a group comprising iridium (Ir), ruthenium (Ru), osmium (Os), platinum (Pt), palladium (Pd) and rhenium (Rh). In a particular embodiment, M is iridium.

In at least one embodiment, the B2 ring is at least one aromatic or heteroaromatic. The B2 ring may be selected from a group comprising at least one fused aromatic, for example naphthalene, an unfused aromatic, for example benzene, a fused heteroaromatic, for example phenanthroline, and an unfused heteroaromatic, for example pyridine. The aromatic and/or heteroaromatic may be substituted or unsubstituted. "Unsubstituted" in respect of the B2 ring here means that the $R_{31}$, $R_{32}$, $R_{33}$, $R_{34}$ radicals are each hydrogen. "Substituted" here and hereinafter means that the rings have substituents other than hydrogen.

The $R_{31}$, $R_{32}$, $R_{33}$, $R_{34}$ radicals may each independently be selected from a group comprising —H, —OH, —$R_{50}$, -phenyl, —$OCOR_{60}$, —$NHCOR_{70}$, —$OR_{80}$, —$NR_{90}R_{100}$, —$NHR_{110}$, —C≡, —C═C, —C═C—, —C and —$NH_2$. The $R_{50}$, $R_{60}$, $R_{70}$, $R_{80}$, $R_{90}$, $R_{100}$, $R_{110}$ radicals may each independently be selected from a group comprising unbranched saturated hydrocarbon chains having one to 20 carbon atoms, for example ethyl, branched saturated hydrocarbon chains having one to 20 carbon atoms, for example tert-butyl, unbranched unsaturated hydrocarbon chains having one to 20 carbon atoms, for example vinyl, branched unsaturated hydrocarbon chains having one to 20 carbon atoms, for example 4-methyl-1-hepten-5-ynyl, aromatic rings, for example benzyl, and nonaromatic rings, for example cyclopentyl.

Alternatively or additionally, the aromatics or heteroaromatics may additionally be fused to further aromatic or nonaromatic rings. This is the case especially when adjacent radicals in the B2 ring include the —C═C—, —C≡C, —C, N═C—, —N—C units and are joined to one another indirectly or directly. More particularly, the result in that case is a fused ring structure comprising at least one B2 ring having a carbon. In various embodiments, the fused ring structure in that case is coordinated to transition metal M via a $sp^2$-hybridized carbon atom. The $R_{31}$, $R_{32}$, $R_{33}$, $R_{34}$ radicals may additionally be fused to further aromatic or nonaromatic rings, especially having 3 to 20 carbon atoms.

In at least one embodiment, the B2 ring is a substituted or unsubstituted naphthalene, especially 1-naphthalene or 2-naphthalene. In other words, the $R_{32}$ and $R_{33}$ and/or $R_{32}$ and $R_{31}$ and/or $R_{31}$ and $R_{34}$ radicals may be part of a further aromatic or heteroaromatic fused to the B2 ring and hence form a fused ring structure, i.e. a naphthalene.

More particularly, the $R_{32}$ and $R_{33}$ substituents of the B2 ring may be fused to form an aromatic system. This forms 1-naphthalene comprising the B2 ring.

Alternatively, the $R_{31}$ and $R_{32}$ radicals of the B2 ring may be fused to form an aromatic system. This forms 2-naphthalene comprising the B2 ring.

In at least one embodiment, the B2 ring is a substituted or unsubstituted phenanthrene. This means, more particularly, that the B2 ring is part of a phenanthrene. In various embodiments, the $R_{32}$ and $R_{33}$ substituents form a further fused aromatic system which may be substituted or unsubstituted. The $R_{31}$ and $R_{34}$ substituents form a further aromatic system fused to the B2 ring. These two further aromatic systems and the B2 ring ultimately form the phenanthrene.

In at least one embodiment, the B1 ring is a nitrogen-containing ring. In various embodiments, the B1 ring is a pyridine substituted on the B2 ring. More particularly, the nitrogen of the pyridine is $sp^2$-hybridized and coordinates to the transition metal M.

The nitrogen-containing ring may additionally be fused to further aromatic or nonaromatic rings. It is possible for a fused ring structure to be formed, comprising the B1 and B2 rings.

The B1 ring may be substituted or unsubstituted. "Unsubstituted" here and hereinafter means that the substituents, in the case of the B1 ring, of at least three of the $R_{41}$, $R_{42}$, $R_{43}$ and $R_{44}$ radicals are each hydrogen and the fourth radical is an electron-withdrawing substituent. The $R_{41}$, $R_{42}$, $R_{43}$ and $R_{44}$ substituents selected may be the same or different. The terms "substituent" and "radical" are used synonymously here and hereinafter.

The $R_{41}$, $R_{42}$, $R_{43}$, $R_{44}$ radicals may each be independently selected from a group comprising —H, —I, —Cl, —Br, —F, —$NO_2$, $N^+R_{120}R_{130}R_{140}$, —$SO_3R_{150}$, —CN, —COCl, —$COOR_{160}$, —C═, —C═C, —C≡C—, —C, —$CR_{170}R_{180}$OH, —$CR_{190}$O and —CHO, where at least one of the $R_{41}$, $R_{42}$, $R_{43}$ and $R_{44}$ radicals is at least one electron-withdrawing substituent. The $R_{120}$, $R_{130}$, $R_{140}$, $R_{150}$, $R_{160}$, $R_{170}$, $R_{180}$, $R_{190}$ radicals may each independently be selected from a group comprising unbranched saturated hydrocarbon chain having one to 20 carbon atoms, for example methyl, branched saturated hydrocarbon chains having one to 20 carbon atoms, for example tert-butyl, and cyclic rings having 3 to 20 carbon atoms, for example cyclohexyl. "Cyclic rings having 3 to 20 carbon atoms" here means especially cyclic aromatic or nonaromatic rings, for example cyclohexyl or phenyl.

"Electron-withdrawing substituents" refers here and hereinafter to functional groups that can exert a —I effect, i.e. a negative inductive effect, via a sigma bond. More particularly, electron-withdrawing substituents may be halogens, for example fluorine (—F), chlorine (—Cl), bromine (—Br) or iodine (—I). In various embodiments, the electron-withdrawing substituent is a fluorine. Alternatively, the functional group may exert a -M effect, i.e. a negative mesomeric effect, via a π bond, for example via a nitro group (—$NO_2$). The electron-withdrawing substituent may, for example, also be a CN group.

In at least one embodiment, the $R_{43}$ substituent is a fluorine. In other words, the B1 ring has, in position 4 according to the structural formula III (see below), a fluorine as substituent. In this way, it is possible to increase the stability of the metal complex.

In at least one embodiment, the metal complex has a D1 ring. The D1 ring is at least one nitrogen-containing ring. Alternatively, it is also possible for more than one nitrogen to be part of the D1 ring. The D1 ring may additionally be fused to aromatic or nonaromatic rings. The D1 ring may be substituted or unsubstituted.

D1 ring especially has the $R_{11}$, $R_{12}$, $R_{13}$ and $R_{14}$ radicals. The $R_{11}$ to $R_{14}$ radicals are either each independently selected from a group comprising —H, —OH, —$R_{50}$, -phenyl, —$OCOR_{60}$, —$NHCOR_{70}$, —$OR_{80}$, —$NR_{90}R_{100}$, —$NHR_{110}$, —C═, —C═C, —C≡C—, —C and —$NH_2$ or each independently selected from a group comprising —H, —I, —Cl, —Br, —F, $N^+R_{120}R_{130}R_{140}$, —$SO_3R_{150}$, —CN, —COCl, —$NO_2$, —$COOR_{160}$, —$CR_{170}R_{180}$OH, —$CR_{190}$O and —CHO. The statements made above apply to the $R_{50}$ to $R_{190}$ radicals.

In at least one embodiment, the metal complex has a D2 ring. The D2 ring is at least one nitrogen-containing ring. One nitrogen coordinates to the transition metal in particular and hence forms a coordinate bond. The D2 ring may additionally be fused to aromatic or nonaromatic rings.

The D1 ring may form a fused structure, for example with the D2 ring. In this case, both the D1 ring and the D2 ring are part of a fused ring system. This fused ring system may be joined to the transition metal via at least one nitrogen atom. More particularly, both the D1 ring and the D2 ring coordinate to the transition metal M via their nitrogen atoms. In this case, both nitrogen atoms have $sp^2$ hybridization.

In embodiments, the D1 and/or D2 ring in each case is a quinoline coordinated to the transition metal via the nitrogen of the quinoline.

The D2 ring may be substituted or unsubstituted. The D2 ring may have the $R_{21}$, $R_{22}$, $R_{23}$ and $R_{24}$ radicals. The $R_{21}$ to $R_{24}$ radicals are either each independently selected from a group comprising —H, —OH, —$R_{50}$, -phenyl, —$OCOR_{60}$, —$NHCOR_{70}$, —$OR_{80}$, —$NR_{90}R_{100}$, —$NHR_{110}$, —C═, —C═C, —C≡C—, —C and —$NH_2$ or each independently selected from a group comprising —H, —I, —Cl, —Br, —F, $N^+R_{120}R_{130}R_{140}$, —$SO_3R_{150}$, —CN,

—COCl, —$NO_2$, —$COOR_{160}$, —$CR_{170}R_{180}OH$, —$CR_{190}O$ and —CHO. The statements made above apply to the $R_{50}$ to $R_{190}$ radicals.

In at least one embodiment, the D1 ring and/or the D2 ring is a quinoline or isoquinoline.

In other words, both the D1 ring and the D2 ring may be part of a quinoline or isoquinoline. For example, the D1 ring may have, via the $R_{11}$ and $R_{12}$ radicals, a further aromatic system coordinated to the D1 ring. In this case, the D1 ring forms a quinoline with the further aromatic system. Alternatively, a further aromatic system may be coordinated to the D1 ring via the $R_{12}$ and $R_{13}$ radicals. The D1 ring is thus part of an isoquinoline. This applies correspondingly to the D2 ring. In this case, a further aromatic system fused to the D2 ring forms a quinoline via the $R_{24}$ and $R_{23}$ radicals. A further aromatic system fused to the D2 ring forms an isoquinoline via the $R_{23}$ and $R_{22}$ radicals.

The quinoline formation of the D1 and D2 rings is also shown in the structural formula II (see below).

The metal complex of the following structural formula III especially shows the nomenclature used according to the application for the positions of the individual atoms in the corresponding B1, B2, D1 and/or D2 rings:

More particularly, the B1, B2, D1, D2 rings form a coordinate bond to the transition metal complex M at their respective 2 positions. More particularly, the B1 and B2 rings are joined to one another at least via their respective 1 positions. Correspondingly, the D1 and D2 rings are joined to one another via their respective 1 positions. The electron-withdrawing substituent is especially disposed at position 4 of the B1 ring. Alternatively, further electron-withdrawing substituents, preferably fluorine, may be attached at positions 3, 5 or 6 of the B1 ring.

The metal complex of the structural formula IV is shown below.

The structural formula IV shows that the atoms of the B1, B2, D1 and/or D2 rings need not necessarily have carbon atoms where they had carbon atoms according to structural formula I. For example, $B_{11}$, $B_{12}$, $B_{13}$, $B_{14}$, $B_{15}$, $B_{21}$, $B_{22}$, $B_{23}$, $B_{24}$, $B_{25}$, $B_{26}$, $D_{11}$, $D_{12}$, $D_{13}$, $D_{14}$, $D_{15}$, $D_{21}$, $D_{22}$, $D_{23}$, $D_{24}$, $D_{25}$ may be independently selected from nitrogen and carbon. More particularly, the B2 ring, as shown in the structural formula I, need not necessarily have carbon atoms at positions 1 to 6. Optionally, the B2 ring may also have nitrogen atoms at positions 1, 2, 3, 4, 5 and/or 6. More particularly, $B_{22}$ is a carbon, in order not to alter the charge of M, since the ligands that are formed by the B1 and B2 rings are anionic ligands.

In at least one embodiment, $A^-$ is a monovalent anion. In other words, $A^-$ in particular is a singly negatively charged atom or molecule. More particularly, the monovalent anion is selected from a group including the following negatively charged elements or compounds: fluorine ($F^-$), chlorine ($Cl^-$), bromine ($Br^-$), iodine ($I^-$), $NO_3^-$, $NO_2^-$, $BF_4^-$, $PF_6^-$, $CF_3SO_3^-$, $CH_3SO_3^-$, $Tf_2N^-$ (trifluoromethylsulfonimide). In a particular embodiment, $A^-$ is a tetrafluorobromide ($BF_4^-$) or hexafluorophosphate ($PF_6^-$).

In at least one embodiment, the metal complex is ionic. What this means is that the central atom and the B1, B2, D1 and D2 rings form a positively charged molecule, i.e. a cation. Thus, it has a positive net charge. This positive net charge can be compensated for by a counterion, especially by the monovalent anion.

In at least one embodiment, the metal complex is set up to emit radiation from the red to deep red spectral region. The red spectral region refers here and hereinafter to a wavelength range from 600 to 635 nm, for example 632 nm. The deep red spectral region refers here and hereinafter to a wavelength range from 636 nm to 685 nm, for example 656 nm.

In at least one embodiment, the metal complex has an emission maximum at a wavelength of 658+/−26 nm. More particularly, the excitation of the metal complex is effected in the UV spectral range, especially between 350 and 380 nm.

In at least one embodiment, the metal complex has the following structural formula II:

where:
$R_{43}$ is —F, —CN or —$NO_2$,
$R_{51}$, $R_{52}$, $R_{53}$, $R_{54}$, $R_{61}$, $R_{62}$, $R_{63}$, $R_{64}$ are each hydrogen, and
M, the B2 ring, the B1 ring, the D1 ring and/or the D2 ring, $A^-$, $R_{41}$, $R_{42}$, $R_{44}$, $R_{31}$, $R_{32}$, $R_{33}$, $R_{34}$, $R_{13}$, $R_{14}$, $R_{21}$, $R_{22}$ are as defined in the structural formula I.

Alternatively, $R_{51}$, $R_{52}$, $R_{53}$, $R_{54}$, $R_{61}$, $R_{62}$, $R_{63}$, $R_{64}$ may be radicals other than hydrogen, for example analogously to the radicals of $R_{23}$ or $R_{13}$.

In this context, all the definitions and embodiments cited above for the metal complex of the structural formulae I, III and IV also apply to the metal complex of the structural formula II, and vice versa.

In at least one embodiment, the metal complex of the structural formula II has a fluorine as the $R_{43}$ radical.

In at least one embodiment, the B2 ring of the metal complex of the structural formula II is part of a naphthalene. More particularly, the naphthalene is substituted or unsubstituted. Possible substituents include, for example, the same radicals as for $R_{23}$ or $R_{13}$.

In at least one embodiment, the B2 ring of the metal complex of the structural formula II is part of a substituted or unsubstituted phenanthrene.

In at least one embodiment, the B1 and B2 rings of the metal complex of the structural formula II or I form a bidentate ligand. More particularly, this bidentate ligand is a monoanionic ligand coordinated to the transition metal M. More particularly, this bidentate ligand coordinates to the transition metal M via a carbon atom of the B2 ring and via a nitrogen atom of the B1 ring. These ligands are preferably referred to as cyclometallizing ligands. In addition, the D1 and D2 rings form a bidentate ligand which can also be referred to as a chelated bidentate diimide ligand. This bidentate ligand comprises at least the D1 ring and also the D2 ring. More particularly, this bidentate ligand coordinates to the transition metal M via at least one nitrogen atom of the D1 ring and via a nitrogen atom of the D2 ring.

It has been found that the highest occupied molecular orbital (HOMO) of a metal complex of the structural formula I is at least partly on the B2 ring, and the lowest unoccupied molecular orbital (LUMO) is completely on the bidentate diimide ligand comprising the D1 ring and the D2 ring. Both bidentate ligands exhibit an advantageous emission process.

In at least one embodiment, the metal complex has the structural formula II. More particularly, the $R_{43}$ radical is an electron-withdrawing substituent, especially fluorine. The other radicals of the B2, B1, D2 and D1 ring may each be hydrogen. The result is a metal complex of the structural formula V which follows. The structural formula V shows, by way of example, iridium as transition metal M and $[PF_6]^-$ as monovalent anion $A^-$.

The metal complex of the structural formula V may be referred to as [iridium(3-fluoro-6-phenylpyridinato)2(2,2'-biquinoline)]$PF_6$.

In at least one embodiment, the metal complex has the structural formula II. More particularly, the $R_{21}$, $R_{22}$, $R_{61}$, $R_{62}$, $R_{63}$, $R_{64}$, $R_{14}$, $R_{13}$, $R_{51}$, $R_{52}$, $R_{53}$ and $R_{54}$ radicals may each be hydrogen. The B2 ring may form a naphthalene. The $R_{43}$ substituent of the B1 ring may be an electron-withdrawing substituent, especially fluorine. The $R_{44}$, $R_{42}$, $R_{41}$ radicals may each be hydrogen. The result is a structural formula VI which shows, by way of example, iridium as transition metal M and $[PF_6]^-$ as monovalent anion $A^-$.

$PF_6^-$ and Ir in the structural formula VI here are merely examples and may also be replaced by other transition metals M or monovalent anions $A^-$. Instead of F, it is also possible to use another electron-withdrawing substituent.

The metal complex of the structural formula VI may be referred to as [iridium(3-fluoro-6-(1-naphthyl)pyridinato)2 (2,2'-biquinoline)]$PF_6$.

In at least one embodiment, the metal complex has the structural formula II. More particularly, the D1 and D2 rings each form an unsubstituted quinoline. The B2 ring especially forms a naphthalene. More particularly, the B2 ring is part of the naphthalene. In this case, more particularly, the $R_{31}$ and $R_{32}$ radicals are used to form a further fused aromatic system. The other $R_{34}$, $R_{33}$, $R_{41}$, $R_{42}$, $R_{44}$ radicals may each be hydrogen. The $R_{43}$ radical is an electron-withdrawing substituent, especially fluorine. The result is a metal complex of the structural formula VII which shows, by way of example, iridium as transition metal and $[PF_6]^-$ as monovalent anion.

$PF6^-$ and Ir in the structural formula V here are merely examples and may also be replaced by other transition metals M or monovalent anions A. Instead of F, it is also possible to use another electron-withdrawing substituent.

$PF6^-$ and Ir in the structural formula VII here are merely examples and may also be replaced by other transition metals M or monovalent anions A⁻. Instead of F, it is also possible to use another electron-withdrawing substituent.

The metal complex of the structural formula VII may be referred to as [iridium(3-fluoro-6-(2-naphthyl)pyridinato)2 (2,2'-biquinoline)]$PF_6$.

In at least one embodiment, the metal complex has the structural formula II. The D2 and D1 rings each form a quinoline. The quinoline is especially unsubstituted. The B1 radical is especially a fluorinated pyridine. More particularly, the electron-withdrawing substituent is arranged at position 4 of the pyridine ring (B1 ring) according to the structural formula III. The B2 ring is part of a phenanthrene. The result is a metal complex of the structural formula VIII which shows, by way of example, iridium as transition metal and [$PF_6$]⁻ as monovalent anion.

$PF_6^-$ and Ir in the structural formula VIII here are merely examples and may also be replaced by other transition metals M or monovalent anions A⁻. Instead of F, it is also possible to use another electron-withdrawing substituent.

The metal complex of the structural formula VIII may be referred to as [iridium(3-fluoro-6-(5-phenanthrene)pyridinato)2(2,2'-biquinoline)]$PF_6$.

In at least one embodiment, the metal complex has the structural formula I. The D2 and D1 rings each form a pyridine. The pyridine of the D2 ring is especially unsubstituted except for the $R_{24}$ radical, which is especially a phenyl. The B1 radical is especially a fluorinated pyridine radical. More particularly, the electron-withdrawing substituent is arranged at position 4 of the pyridine ring (B1 ring) according to the structural formula III. The B2 ring is part of a phenanthrene. The result is a metal complex of the structural formula IX which shows, by way of example, iridium as transition metal and [$PF_6$]⁻ as monovalent anion.

$PF_6^-$ and Ir in the structural formula IX here are merely examples and may also be replaced by other transition metals M or monovalent anions A. Instead of F, it is also possible to use another electron-withdrawing substituent.

The metal complex of the structural formula VIII may be referred to as [iridium(3-fluoro-6-(5-phenanthrene)pyridinato)2(6-phenyl-2,2'-bipyridine)]$PF_6$.

The inventors have recognized that the metal complexes of the structural formulae I to IX have high structural stability. More particularly, the metal complexes have high stability at high temperatures or during the operation of a light-emitting organic component.

In principle, the structural instability of metal complexes is caused by a strong sigma anti-bonding interaction between the transition metal, for example iridium, and a nitrogen atom of the B1/B2 ligand system. This strong anti-bonding interaction between the occupied $e_g$ orbital of the transition metal (iridium) and the unhybridized orbital of the sp² nitrogen of the B1/B2 ligand becomes stronger during the operation of a component. The population of the $e_g$ orbital (³MC level) leads to enhancement of the σ anti-bonding interactions during the operation of the component and hence to significant elongation of the transition metal-nitrogen bond, and as a result causes opening of the molecular structure. The opening of the molecular structure allows small nucleophilic molecules to enter and can lead to degradation, i.e. to breaking, of the transition metal-nitrogen bond (iridium-nitrogen of the B1/B2 ligand system). The degradation is promoted by intermolecular interactions.

It is therefore desirable to provide a metal complex wherein the strong anti-bonding interactions between the unoccupied $e_g$ orbital of the transition metal, for example iridium, and the unhybridized sp² orbital of the nitrogen of the B1/B2 ligand are attenuated by the use of an electron-withdrawing substituent on the B1 ring, especially on the pyridine as B1 ring. This can especially be effected by means of electron-withdrawing substituents such as fluorine, CN, $NO_2$ on the B1 ring, especially when the B1 ring is a pyridine ring.

The invention further relates to a process for preparing a metal complex. In various embodiments, the process prepares the metal complex. Thus, all the definitions and embodiments cited for the metal complex also apply to the process, and vice versa.

This process for preparing a metal complex has the process steps of:

A) providing a transition metal M which is part of a central atom compound, and

B) mixing the central atom compound in ligands dissolved in solvents to form a metal complex, where the ligands comprise the rings B1, B2, D1 and D2, and the rings B1, B2, D1, D2 each form a coordinate bond to the central atom or transition metal.

In at least one embodiment, the metal complex is purified by column chromatography.

For example, a metal complex of the structural formula I can be prepared as follows:

Ligand Synthesis

Ligands comprising at least the B1 and B2 rings can be prepared by a Suzuki coupling, as shown, for example, in L. Chun et al., Eur. J. Org. Chem., 2010, 29, pages 5548 to 5551. The disclosure content relating to the preparation in Chun et al. is hereby incorporated by reference. To a mixture of fluorinated 2-pyridyl bromide (for example 2-bromo-5-fluoropyridine, 1 eq.), potassium phosphate (2 eq.) and Pd(OAc)₂ (0.5 mol % of 1 eq.) in ethylene glycol is added an appropriate proportion of arylboronic acid (1.3 eq.). The mixture is boiled under reflux at 80° C. for 24 hours. The mixture can be cooled down to room temperature. Subsequently, a salt solution can be added and the mixture can be extracted with diethyl ether. The contents in the ether can be concentrated and the crude ligand can be obtained as a viscous liquid. The ligands are purified by column chromatography. A colorless liquid or a white powder is formed.

The preparation of the ligands is also illustrated in the reaction equations which follow.

Example

$R_1$ in these equations denotes the $R_{31}$ to $R_{34}$ radicals. $R_2$ in these equations denotes the $R_{41}$ to $R_{44}$ radicals. Z means here that at least one $R_{41}$ to $R_{44}$ radical is an electron-withdrawing substituent.

Chlorine-Bridged Intermediate of Diiridium Complexes

Chlorine-bridged dimetallic complexes can be synthesized as published in E. Holder et al., 2005, Adv. Mater. 2005, 17, pages 1109-1121. The disclosure content of Holder et al. in relation to the synthesis is hereby incorporated by reference. $IrCl_3 \cdot xH_2O$ (i eq.) is introduced into a Schlenk vessel in an argon glovebox. Water and 2-methoxyethanol are added. This can be effected by means of a cannula. During this, the reaction mixture is stirred. The required ligands comprising the B1 and B2 rings (2.15 eq.) are added and this reaction mixture is boiled at 120° C. for 18 hours under pressure-regulating conditions and reflux. The mixture can be cooled down to room temperature and precipitated. The precipitate is filtered and washed in water and diethyl ether. The precipitate formed is subsequently dried under reduced pressure. The synthesis and the operations are conducted under inert gas atmosphere. The following schemes show the preparation of these intermediate complexes by way of example:

Example

Ionic Heteroleptic Iridium Complexes

Metal complexes, especially light-emitting ionic iridium complexes, are synthesized as disclosed in J. D. Slinker et al., J. Am. Chem. Soc., 2004, 126, pages 2736-2767. The disclosure content of Slinker et al. in relation to the synthesis is hereby incorporated by reference. The required proportions of the ligands comprising the D1 and D2 rings (2.15 eq.) and the chlorine-bridged iridium dimers (i eq.) are transferred into a Schlenk vessel in an argon glovebox. Ethylene glycol is added, for example by means of a cannula, and the reaction mixture is boiled at 150° C. for 20 hours (under reflux and pressure-regulating conditions). This forms a clear solution. The solution can be cooled down to room temperature and introduced into another Schlenk vessel comprising distilled water. The excess of the aqueous solution of ammonium hexafluorophosphate ($NH_4PF_6$) is added to this aqueous solution, so as to result in an intermediate as precipitate of the desired heteroleptic iridium complex. The product is filtered and washed with water and diethyl ether and then dried under reduced pressure. The synthesized complex is purified by means of column chromatography. The product obtained is dried under reduced pressure. The synthesis, the operations and the purification are conducted under inert gas atmosphere. The following diagram shows the preparation of an ionic heteroleptic iridium complex:

Example

Additionally specified is an organic light-emitting component. Preferably, the organic light-emitting component includes the metal complex. This means that all the definitions and embodiments cited for the metal complex also apply to the component, and vice versa.

In at least one embodiment, the organic light-emitting component has at least one organic light-emitting layer between two electrodes. The organic light-emitting layer includes a metal complex, preferably the above-described metal complex, as emitter material.

In at least one embodiment, the organic light-emitting component is an organic light-emitting diode (OLED). Alternatively, the organic light-emitting component may be an organic light-emitting electrochemical cell (OLEEC). The organic light-emitting component has at least one organic light-emitting layer.

An organic light-emitting electrochemical cell generally differs from an organic light-emitting diode in that the electrochemical cell has just one organic light-emitting layer between the two electrodes. In other words, the electrochemical cell does not have any further layers, especially injection layers, transport layers and/or blocker layers. Thus, the organic light-emitting electrochemical cell has a simpler structure compared to an organic light-emitting diode. By contrast, the organic light-emitting diode generally has a functional layer stack.

The functional layer stack may include layers comprising organic polymers, organic oligomers, organic monomers, organic small non-polymeric molecules ("small molecules") or combinations thereof. The functional layer stack may have, in addition to the at least one organic light-emitting layer, a further functional layer executed in the form of a hole transport layer, in order to enable effective hole injection into at least the organic light-emitting layer. Advantageous materials for a hole transport layer may be found, for example, to be tertiary amines, carbazole derivatives, camphorsulfonic acid-doped polyaniline or polystyrenesulfonic acid-doped polyethylenedioxythiophene. The functional layer stack may further include at least one functional layer which takes the form of an electron transport layer. In general, the functional layer stack may have, in addition to the organic light-emitting layer, further layers selected from hole injection layers, hole transport layers, electron injection layers, electron transport layers, hole blocker layers and electron blocker layers.

In at least one embodiment, the organic light-emitting component has at least two electrodes. More particularly, the functional layer stack is arranged between the two electrodes.

In at least one embodiment, at least one of the electrodes is transparent. "Transparent" refers here and hereinafter to a layer which is transparent in respect of visible light. The transparent layer may be clear and translucent or at least partly light-scattering and/or partly light-absorbing, such that the transparent layer may, for example, also have diffuse or milky translucency. In a particular embodiment, a layer referred to here as transparent has maximum transparency, such that, more particularly, the absorption of the light or radiation generated in the functional layer stack in the course of operation of the component is as small as possible.

In at least one embodiment, both electrodes are transparent. Thus, the light generated in the organic light-emitting layer can be emitted in both directions, i.e. through both electrodes. In other words, the device is a transparent OLED or OLEEC. Alternatively, the light can also be emitted in just one direction, for example through an electrode facing the substrate. In this case, reference is also made to a bottom emitter. If the light is emitted through the electrode facing away from the substrate, reference is also made to a top emitter.

The material used for a transparent electrode may, for example, be a transparent conductive oxide. Transparent conductive oxides ("TCOs" for short) are generally metal oxides, for example zinc oxide, tin oxide, cadmium oxide, titanium oxide, indium oxide or indium tin oxide (ITO). As well as binary metal-oxygen compounds, for example ZnO, $SnO_2$ or $In_2O_3$, the group of the TCOs also includes ternary metal-oxygen compounds, for example $Zn_2SnO_4$, $CdSnO_3$, $ZnSnO_3$, $MgIn_2O_4$, $GaInO_3$, $Zn_2In_2O_5$ or $In_4Sn_3O_{12}$, or mixtures of different transparent conductive oxides. At the same time, the TCOs do not necessarily correspond to a stoichiometric composition and may additionally be p- or n-doped. More particularly, the transparent material is indium tin oxide (ITO).

The second electrode, which is especially in non-transparent form, may, for example, be the cathode and may consist of or comprise aluminum, barium, indium, silver, gold, magnesium, calcium or lithium, and combinations or alloys thereof. The material for the second electrode is especially air-stable and/or non-reactive. It is thus possible to dispense with hermetic sealing of the organic light-emitting component. This saves costs and time in the production of the organic light-emitting component.

In at least one embodiment, the organic light-emitting layer is arranged in direct contact with the first electrode and with the second electrode. "Direct contact" is understood here to mean especially direct mechanical and/or electrical contact.

In at least one embodiment, the organic light-emitting component has a substrate. More particularly, one of the two electrodes is disposed on the substrate. The substrate may, for example, include one or more materials in the form of a layer, a sheet, a film or a laminate, these being selected from glass, quartz, plastic, metal, silicon, wafer. More particularly, the substrate includes or consists of glass.

In at least one embodiment, the component is set up, especially set up in operation, to emit radiation from the red or deep red spectral region. In various embodiments, the dominant wavelength of the red wavelength range has a value of 620 nm with a tolerance of 20 nm from this value. In some embodiments, the dominant wavelength of the deep red wavelength range has a value of 660 nm with a tolerance of 20 nm from this value. Dominant wavelength refers to the wavelength that describes the hue of an OLED or LEC as perceived by the human eye.

In at least one embodiment, the organic light-emitting component has an encapsulation. In embodiments, the encapsulation is applied in the form of a thin-film encapsulation to the organic light-emitting component. More particularly, the encapsulation protects the functional layer stack or at least the organic light-emitting layer and the electrodes from the environment, for example from moisture and/or oxygen and/or other corrosive substances, for instance hydrogen sulfide. The encapsulation may include one or more thin layers applied, for example, by means of chemical vapor deposition (CVD). For example, the encapsulation may be a glass lid that has been stuck on.

The inventors have recognized that the metal complex of at least the structural formula I can provide an efficient and inexpensive emitter material for an organic light-emitting component. More particularly, the organic light-emitting component may have a flexible size. The organic light-emitting component can be employed in packaging or lighting.

In at least one embodiment, the organic light-emitting layer may have been produced from the liquid phase. More particularly, the treatment can be effected by a solution-based process, such as a roll-to-roll process, spin-coating or printing method.

In at least one embodiment, the organic light-emitting layer has been produced from the liquid phase, and the metal complex is homogeneously distributed in a matrix material. Alternatively, the metal complex may also have a concentration gradient in the matrix material. The matrix material may, for example, be TCTA, tris(4-carbazol-9-yl)triphenylamine, or CBP, 4,4'-bis(N-carbazolyl)-1,1'-biphenyl.

In at least one embodiment, the matrix material includes further additional materials which may be uncharged or have an ionic charge. For example, the further material may be an ionic liquid. Ionic liquids used may, for example, be 1-butyl-3-methylimidazolium hexafluorophosphate.

In at least one embodiment, the metal complex is distributed within the matrix material at least to an extent of 60% by weight, especially to an extent of 80% by weight, preferably more than 90% by weight.

BRIEF DESCRIPTION OF THE DRAWINGS

Further advantages, advantageous embodiments and developments will be apparent from the working examples described hereinafter in conjunction with the figures.

The figures show.

Each of FIGS. 3A to 3D an emission spectrum of one embodiment.

In the working examples and figures, elements that are identical or of the same type or have the same effect may each be given the same reference signs. The elements shown and their size ratios relative to one another should not be regarded as being to scale. Instead, individual elements, for example layers, parts, components and regions, may be shown in excessively large size for better reproducibility and/or for better understanding.

DETAILED DESCRIPTION OF ILLUSTRATIVE EMBODIMENTS

Figure 1:
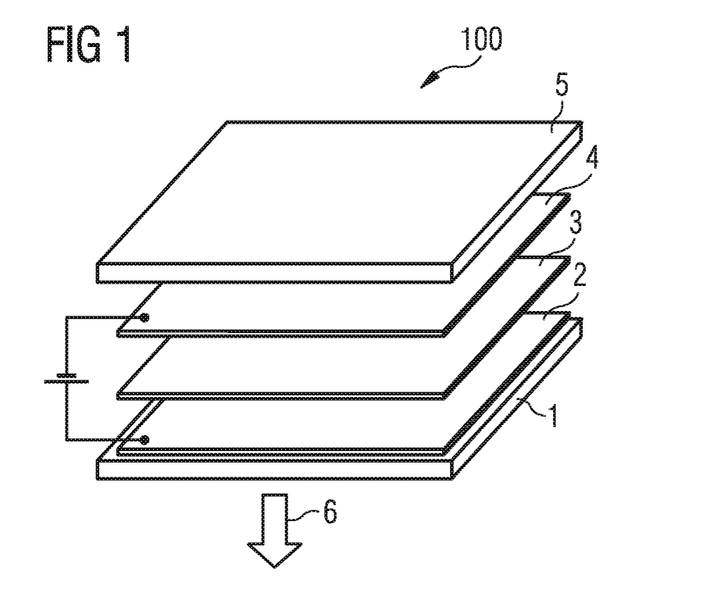
FIG. 1 a schematic side view of an organic light-emitting component in one embodiment.

FIG. 1 shows a schematic side view of an optoelectronic component in one embodiment. The organic light-emitting component 100 has a substrate 1. The substrate 1 may be formed, for example, from glass. A first electrode 2 is arranged directly alongside the substrate 1. The first electrode 2 may be formed, for example, from a transparent conductive material, for example ITO. More particularly, the first electrode 2 has a layer thickness of 100 to 150 nm. The first electrode 2 is followed by an organic light-emitting layer 3. The organic light-emitting layer 3 includes the metal complex as emitter material. The metal complex may be embedded in a matrix material. The embedding can be effected in a homogeneous manner or by means of a concentration gradient. The organic light-emitting layer 3 is followed by a second electrode 4. The second electrode 4 may, for example, be in reflective form. The second electrode 4 may have a layer thickness, for example, of 130 nm. More particularly, only the organic light-emitting layer 3 is arranged between the first electrode 2 and the second electrode 4, and so no further layers are arranged therebetween. In other words, the organic light-emitting component takes the form of an organic light-emitting electrochemical cell (OLEEC). The second electrode 4 may be followed by an encapsulation 5. More particularly, the organic light-emitting component 100 may take the form of a bottom emitter. In other words, the radiation generated in the organic light-emitting layer 3 is emitted in the direction of the first electrode 2 via the first substrate 1 (arrow 6).

Figure 2:
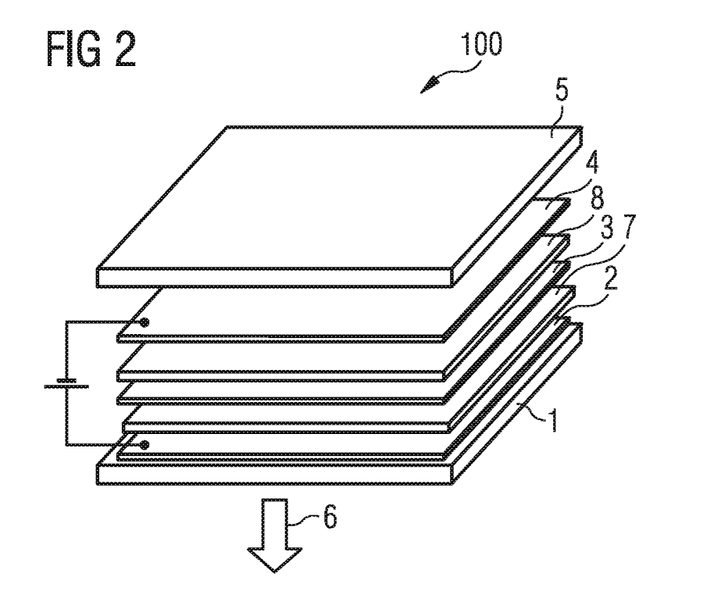
FIG. 2 a schematic side view of an organic light-emitting component in one embodiment.

FIG. 2 shows a schematic side view of an organic light-emitting component in one embodiment. The organic light-emitting component 100 of FIG. 2 differs from the organic light-emitting component 100 of FIG. 1 in that it has further layers between the first electrode 2 and the second electrode 4. More particularly, a further layer 7 is arranged between the first electrode 2 and the organic light-emitting layer 3. For example, the further layer 7 may be a hole injection layer. A further layer 8, for example an electron transport layer, may be arranged between the organic light-emitting layer 3 and the second electrode 4. More particularly, the component 100 according to FIG. 2 is an OLED. Alternatively, the components 100 in FIGS. 1 and 2 may also take the form of top emitters or of transparent components.

Figure 3A:
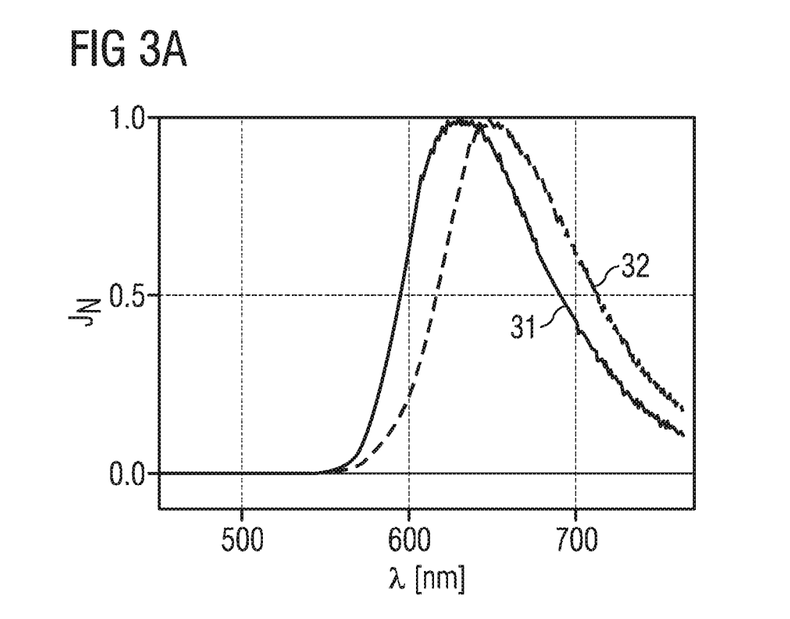

FIG. 3A shows an emission spectrum of two working examples. The emission spectrum shows the normalized intensity $I_N$ as a function of the wavelength $\lambda$ in nm in the form of a graph. The graph 31 shows the metal complex [iridium(3-fluoro-6-(1-naphthyl)pyridinato)2(2,2'-biquinoline)]$PF_6$. The graph 32 shows the emission spectrum of the metal complex [iridium(3-fluoro-6-(2-naphthyl)pyridinato)2(2,2'-biquinoline)]$PF_6$. The metal complex of the graph 31 accordingly corresponds to the structural formula VI, and the metal complex of the graph 32 corresponds to the structural formula VII. It is apparent from the graph that the metal complex of the structural formula VII has a wavelength maximum at about 65 nm (graph 32). The metal complex of the structural formula VI has a wavelength maximum of about 632 nm (graph 31). Thus, both metal complexes emit in the red to deep red spectral region. Excitation was effected in the UV region, especially at 360 nm.

Figure 3B:
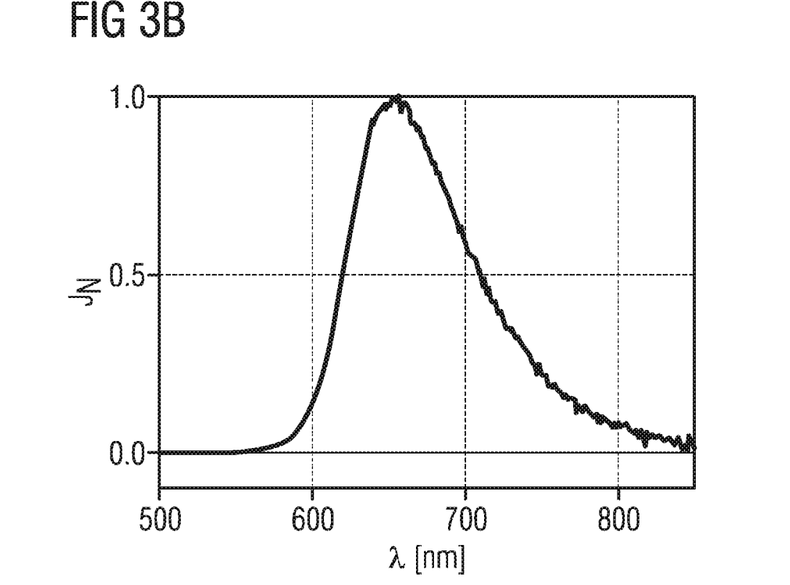

FIG. 3B shows the emission spectrum of [iridium(3-fluoro-6-phenylpyridinato)2(2,2'-biquinoline)$PF_6$, i.e. the metal complex of the structural formula V. What is shown is the normalized intensity $I_N$ as a function of the wavelength $\lambda$ in nm. The metal complex of the structural formula V shows an emission maximum at about 656 nm. Excitation was effected in the UV region, especially at 360 nm.

Figure 3C:
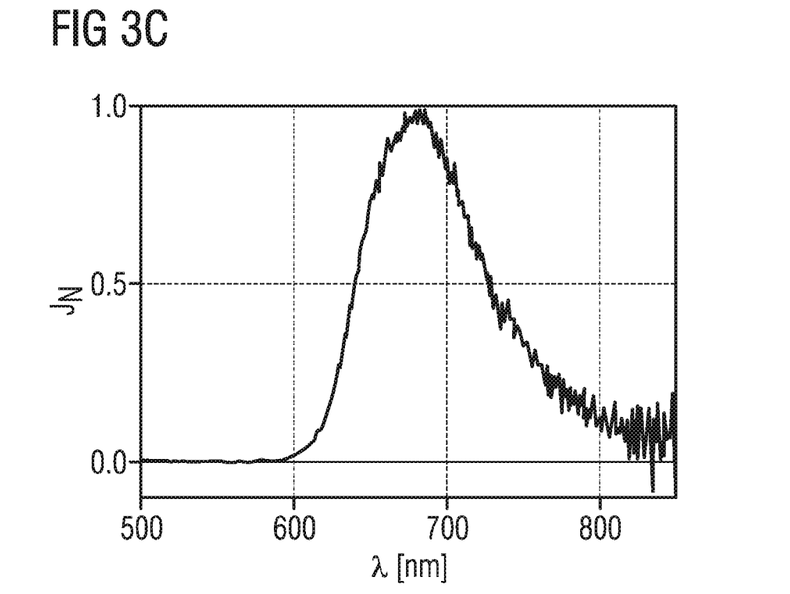

FIG. 3C shows an emission spectrum of the metal complex [iridium(3-fluoro-6-(5-phenanthrene)pyridinato)2(2,2'-biquinoline)$PF_6$, i.e. the metal complex of the structural formula VIII. What is shown is the normalized intensity $I_N$ as a function of the wavelength $\lambda$ in nm. The metal complex of the structural formula VIII shows an emission maximum at about 683 nm. Excitation was effected in the UV region, especially at 360 nm.

Figure 3D:
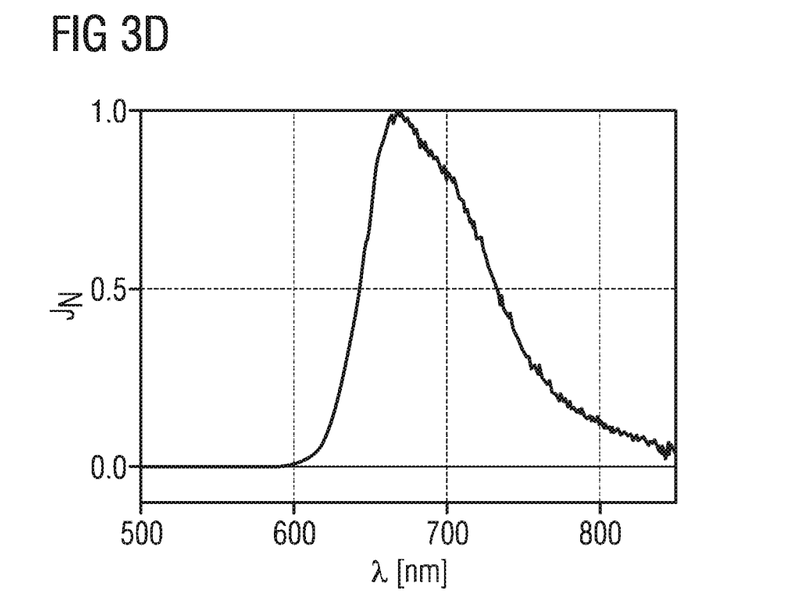

FIG. 3D shows the emission spectrum of [iridium(3-fluoro-6-(5-phenanthrene)pyridinato)2(6-phenyl-2,2'-bipyridine)$PF_6$, i.e. the metal complex of the structural formula IX. What is shown is the normalized intensity $I_N$ as a function of the wavelength $\lambda$ in nm. The metal complex of the structural formula IX shows a wavelength maximum at about 667 nm. Excitation was effected in the UV region, especially at 360 nm.

It is apparent from the graphs of FIGS. 3A to 3D that the metal complexes of the structural formulae V to IX all emit in the red to deep red spectral region.

Figure 4:
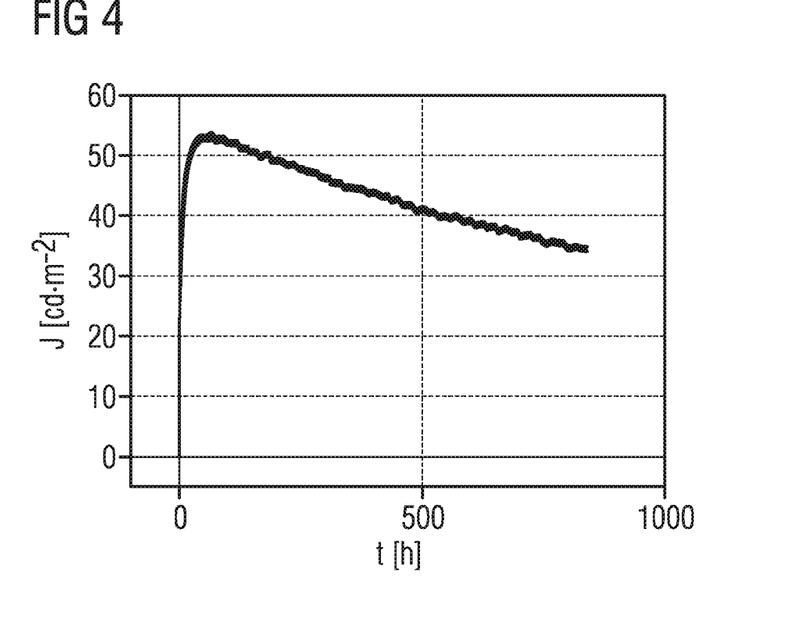
FIG. 4 the luminescence as a function of time in one embodiment.

FIG. 4 shows the luminescence L in cd/m$^2$ as a function of time t in hours h of [iridium(3-fluoro-6-phenylpyridinato)2(2,2'-biquinoline)]$PF_6$, i.e. the metal complex of the structural formula V. It is apparent from the graph that the luminescence decreases only slightly with increasing time. Thus, the metal complex has excellent luminescence stability over time.

Figure 5:
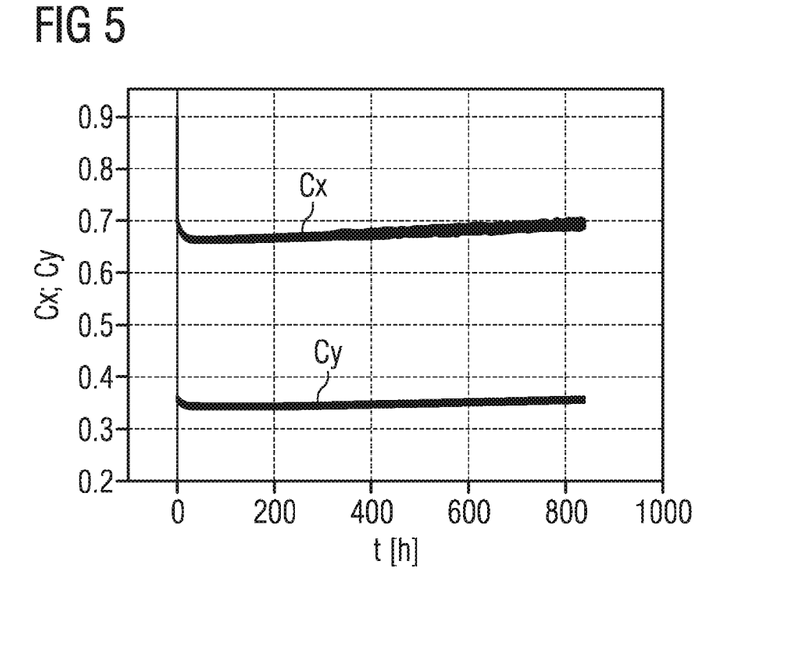
FIG. 5 the color locus coordinates in one embodiment.

FIG. 5 shows the color locus coordinates Cx and Cy of the metal complex [iridium(3-fluoro-6-phenylpyridinato)2(2,2'-biquinoline)]$PF_6$, i.e. the metal complex of the structural formula V. What are shown are the color locus coordinates Cx and Cy as a function of time t in hours h. It is apparent from the graph that neither the Cx coordinate nor the Cy coordinate changes over time. In other words, the metal complex exhibits a stable color locus over time. The color locus is in the red spectral region.

The working examples described in conjunction with the figures and the features thereof may also be combined with one another in further working examples, even when such combinations are not shown explicitly in the figures. In addition, the working examples described in conjunction with the figures may have additional or alternative features according to the description in the general part.

The invention is not restricted to the working examples by their citation in the description. Instead, the invention encompasses every novel feature and every combination of features, especially including every combination of features in the claims, even when this feature or this combination itself is not specified explicitly in the claims or working examples.

The invention claimed is:

1. A metal complex having the structural formula I:

where:
M is a transition metal having an atomic number greater than 40,
a B2 ring is a substituted phenyl ring,
a B1 ring, a D1 ring and a D2 ring are each pyridine, the B2 ring, the D1 ring and/or the D2 ring are joinable together to form fused aromatic and/or heteroaromatic rings,
$A^-$ is a monovalent anion,
$R_{31}, R_{32}, R_{33}, R_{34}$ are each independently selected from the group consisting of H, —OH, —$R_{50}$, -phenyl, —$OCOR_{60}$, —$NHCOR_{70}$, —$OR_{80}$, —$NR_{90}R_{100}$, —$NHR_{110}$ and —$NH_2$,
wherein $R_{50}, R_{60}, R_{70}, R_{80}, R_{90}, R_{100}, R_{110}$ are each independently selected from the group consisting of unbranched saturated hydrocarbon chains having 1 to 20 carbon atoms, branched saturated hydrocarbon chains having 1 to 20 carbon atoms, unbranched unsaturated hydrocarbon chains having 1 to 20 carbon atoms, branched unsaturated hydrocarbon chains having 1 to 20 carbon atoms, aromatic rings and nonaromatic rings,
wherein $R_{41}, R_{42}, R_{43}, R_{44}$ are each independently selected from the group consisting of —H, —I, —Cl, —Br, —F, —$NO_2$, $N^+R_{120}R_{130}R_{140}$, —$SO_3R_{150}$, —CN, —COCl, —$COOR_{160}$, —$CR_{170}R_{180}OH$, —$CR_{190}O$ and —CHO,
wherein at least one of the $R_{41}, R_{42}, R_{43}$ and $R_{44}$ radicals is at least one electron-withdrawing substituent, wherein the electron-withdrawing substituent is selected from the group consisting of —F, —CN and —$NO_2$,
wherein $R_{120}, R_{130}, R_{140}, R_{150}, R_{160}, R_{170}, R_{180}, R_{190}$ are each independently selected from the group consisting of unbranched saturated hydrocarbon chains having 1 to 20 carbon atoms, branched saturated hydrocarbon chains having 1 to 20 carbon atoms and cyclic rings having 3 to 20 carbon atoms,
wherein $R_{11}, R_{12}, R_{13}, R_{14}, R_{21}, R_{22}, R_{23}, R_{24}$ are either each independently selected from the group consisting of —H, —OH, —$R_{50}$, -phenyl, —$OCOR_{60}$, —$NHCOR_{70}$, —$OR_{80}$, —$NR_{90}R_{100}$, —$NHR_{110}$ and —$NH_2$ or each independently selected from the group consisting of —H, —I, —Cl, —Br, —F, $N^+R_{120}R_{130}R_{140}$, —$SO_3R_{150}$, —CN, —COCl, —$NO_2$, —$COOR_{160}$, —$CR_{170}R_{180}OH$, —$CR_{190}O$ and —CHO, and wherein the metal complex is capable of emitting radiation from a red spectral range having an emission maximum with a wavelength of 658 nm+/−26 nm, the emission maximum being present upon excitation with UV at 360 nm.

2. The metal complex according to claim 1, wherein $R_{43}$ is fluorine.

3. The metal complex according to claim 1, wherein M is selected from the group consisting of Ir, Ru, Os and Pt.

4. An organic light-emitting component comprising:
at least one organic light-emitting layer between two electrodes,
wherein the organic light-emitting layer comprises the metal complex according to claim 1 as an emitter material.

5. The organic light-emitting component according to claim 4, wherein the organic light-emitting component is an organic light-emitting diode.

6. The organic light-emitting component according to claim 4, wherein the organic light-emitting component is an organic light-emitting electrochemical cell.

7. The organic light-emitting component according to claim 4, wherein the organic light-emitting layer has been produced from a liquid phase, and wherein the metal complex is homogeneously distributed in a matrix material.

8. The organic light-emitting component according to claim 4, wherein the organic light-emitting component is configured to emit radiation from a red spectral region.

9. A metal complex having the structural formula II:

and wherein
$R_{43}$ is —F, —CN or —NO$_2$,
$R_{51}$, $R_{52}$, $R_{53}$, $R_{54}$, $R_{61}$, $R_{62}$, $R_{63}$, $R_{64}$ are each hydrogen,
M is a transition metal having an atomic number greater than 40,
a B2 ring is a substituted phenyl ring,
a B1 ring, a D1 ring and a D2 ring are each pyridine a nitrogen containing rings, the B2 ring, the D1 ring and/or the D2 ring are joinable together to form fused aromatic and/or heteroaromatic rings,
A$^-$ is a monovalent anion,
$R_{31}$, $R_{32}$, $R_{33}$, $R_{34}$ are each independently selected from the group consisting of —H, —OH, —R$_{50}$, -phenyl, —OCOR$_{60}$, —NHCOR$_{70}$, —OR$_{80}$, —NR$_{90}$R$_{100}$, —NHR$_{110}$, and —NH$_2$,
wherein $R_{50}$, $R_{60}$, $R_{70}$, $R_{80}$, $R_{90}$, $R_{100}$, $R_{110}$ are each independently selected from the group consisting of unbranched saturated hydrocarbon chains having 1 to 20 carbon atoms, branched saturated hydrocarbon chains having 1 to 20 carbon atoms, unbranched unsaturated hydrocarbon chains having 1 to 20 carbon atoms, branched unsaturated hydrocarbon chains having 1 to 20 carbon atoms, aromatic rings and nonaromatic rings,
wherein $R_{41}$, $R_{42}$, $R_{44}$ are each independently selected from the group consisting of —H, —I, —Cl, —Br, —F, —NO$_2$, N$^+$R$_{120}$ R$_{130}$R$_{140}$, —SO$_3$R$_{150}$, —CN, —COCl, —COOR$_{160}$, —CR$_{170}$R$_{180}$OH, —CR$_{190}$O and —CHO,
wherein at least one of the $R_{41}$, $R_{42}$, $R_{43}$ and $R_{44}$ radicals is at least one electron-withdrawing substituent, wherein the electron-withdrawing substituent is selected from the group consisting of —F, —CN and —NO$_2$,
wherein $R_{120}$, $R_{130}$, $R_{140}$, $R_{150}$, $R_{160}$, $R_{170}$, $R_{180}$, $R_{190}$ are each independently selected from the group consisting of unbranched saturated hydrocarbon chains having 1 to 20 carbon atoms, branched saturated hydrocarbon chains having 1 to 20 carbon atoms and cyclic rings having 3 to 20 carbon atoms,
wherein $R_{13}$, $R_{14}$, $R_{21}$, $R_{22}$, are either each independently selected from the group consisting of —H, —OH, —R$_{50}$, -phenyl, —OCOR$_{60}$, —NHCOR$_{70}$, —OR$_{80}$, —NR$_{90}$R$_{100}$, —NHR$_{110}$, and —NH$_2$ or each independently selected from the group consisting of —H, —I, —Cl, —Br, —F, N$^+$R$_{120}$R$_{130}$R$_{140}$, —SO$_3$R$_{150}$, —CN, —COCl, —NO$_2$, —COOR$_{160}$, —CR$_{170}$R$_{180}$OH, —CR$_{190}$O and —CHO, and
wherein the metal complex is capable of emitting radiation from a red spectral range having an emission maximum with a wavelength of 658 nm+/−26 nm, the emission maximum being present upon excitation with UV at 360 nm.

10. The metal complex according to claim 9, wherein the complex is [iridium(3-fluoro-6-(2-naphthyl)pyridinato)2(2,2'-biquinoline)]PF$_6$ or [iridium(3-fluoro-6-phenylpyridinato)2(2,2'-biquinoline)]PF$_6$.

11. The metal complex according to claim 9, wherein the complex is [iridium(3-fluoro-6-(5-phenanthrene)pyridinato)2(2,2'-biquinoline)PF$_6$ or [iridium(3-fluoro-6-(5-phenanthrene)pyridinato)2(6-phenyl-2,2'-bipyridine)PF$_6$.

* * * * *

UNITED STATES PATENT AND TRADEMARK OFFICE
CERTIFICATE OF CORRECTION

PATENT NO. : 10,177,321 B2
APPLICATION NO. : 15/215355
DATED : January 8, 2019
INVENTOR(S) : Jude Eko Namanga et al.

Page 1 of 1

It is certified that error appears in the above-identified patent and that said Letters Patent is hereby corrected as shown below:

In the Claims

In Column 20, Line 31, Claim 1, delete "the group consisting of H," and insert --the group consisting of -H,--.

In Column 21, Lines 55-56, Claim 9, delete "a nitrogen containing rings".

Signed and Sealed this
Nineteenth Day of March, 2019

Andrei Iancu
*Director of the United States Patent and Trademark Office*